US012263309B2

(12) United States Patent
Iverson (10) Patent No.: US 12,263,309 B2
(45) Date of Patent: Apr. 1, 2025

(54) FREQUENCY GENERATOR WITH BIOLOGICAL APPLICATION

(71) Applicant: Andrew Iverson, Yelm, WA (US)

(72) Inventor: Andrew Iverson, Yelm, WA (US)

( * ) Notice: Subject to any disclaimer, the term of this patent is extended or adjusted under 35 U.S.C. 154(b) by 592 days.

(21) Appl. No.: 17/469,141

(22) Filed: Sep. 8, 2021

(65) Prior Publication Data
US 2022/0072266 A1    Mar. 10, 2022

Related U.S. Application Data

(60) Provisional application No. 63/076,245, filed on Sep. 9, 2020.

(51) Int. Cl.
*A61M 21/00*    (2006.01)

(52) U.S. Cl.
CPC ..... *A61M 21/00* (2013.01); *A61M 2021/0027* (2013.01); *A61M 2021/0055* (2013.01); *A61M 2205/584* (2013.01); *A61M 2205/587* (2013.01)

(58) Field of Classification Search
None
See application file for complete search history.

(56) References Cited

U.S. PATENT DOCUMENTS

| | | | | |
|---|---|---|---|---|
| 4,315,502 A | * | 2/1982 | Gorges | A61M 21/00 600/27 |
| 5,984,854 A | | 11/1999 | Ishikawa et al. | |
| 10,688,274 B1 | * | 6/2020 | Jovanov | A61M 21/02 |
| 2010/0331912 A1 | | 12/2010 | Tass et al. | |
| 2011/0005532 A1 | * | 1/2011 | Faubert | G09B 23/28 128/897 |
| 2017/0173481 A1 | | 6/2017 | Nielsen et al. | |
| 2019/0255350 A1 | | 8/2019 | Malchano et al. | |
| 2020/0139113 A1 | * | 5/2020 | Shin | A61N 1/0456 |
| 2020/0246579 A1 | | 8/2020 | Cohen | |
| 2023/0055962 A1 | * | 2/2023 | Phillips | A61N 2/12 |
| 2023/0310792 A1 | * | 10/2023 | Fortkort | A61M 21/00 600/27 |

OTHER PUBLICATIONS

Rodriquez, Kari; International Search Report and Written Opinion; dated Dec. 8, 2021; 9-pages; Alexandria, VA.

* cited by examiner

*Primary Examiner* — Thaddeus B Cox (57) ABSTRACT

A method of delivering stimulation to a subject includes positioning a plurality of speakers so as to face a subject, the speakers capable of producing frequencies under 20 Hz, wrapping a belt around the subject, the belt including a plurality of metal coils arranged thereon so as to face the subject, each of the metal coils operable to produce a time-varying magnetic field in response to an applied signal, positioning eyewear on the subject, the eyewear including one or more opaque surfaces for blocking a wearer's vision and a plurality of light-emitting diodes (LEDs) arranged on the eyewear so as to be directed toward the wearer's eyes, and delivering, from a frequency generator, respective frequency signals to simultaneously drive the plurality of speakers, the plurality of metal coils, and the plurality of LEDs.

10 Claims, 4 Drawing Sheets

FREQUENCY GENERATOR WITH BIOLOGICAL APPLICATION

CROSS-REFERENCE TO RELATED APPLICATIONS

The present application relates to and claims the benefit of U.S. Provisional Application No. 63/076,245, filed Sep. 9, 2020, the entire disclosure of which is hereby wholly incorporated by reference.

STATEMENT RE: FEDERALLY SPONSORED RESEARCH/DEVELOPMENT

Not Applicable

BACKGROUND

While the basic biological need for adequate sleep is widely recognized, the profound health benefits of rest and relaxation are less so. Despite well documented evidence that wakeful rest can reduce stress and pain, lower blood pressure, and improve various other aspects of a person's health, most people are forced to forgo these benefits in the pursuit of their careers and other responsibilities of their daily lives. There is also no general consensus as to which restful and relaxing activities most profoundly impact a person's wellbeing and thus allow the person to get the most out of a relaxation session. A person is left with a wide range of options, including stretching exercises, breathing exercises, meditation, massage, listening to soothing music, or just lying on the couch. Unfortunately, conventional rest and relaxation techniques, though each may have certain benefits on its own, do not generally work together as a cohesive regimen. As such, conventional techniques do not take advantage of the natural harmonies that can exist between simultaneously experienced sensory stimuli, and the health benefits of such natural harmonies go unrealized.

BRIEF SUMMARY

The present disclosure contemplates various systems, methods, and apparatuses for overcoming the above drawbacks accompanying the related art. One aspect of the embodiments of the present disclosure is a system for delivering stimulation to a subject. The system may comprise a plurality of speakers capable of producing frequencies under 20 Hz, a belt including a plurality of metal coils arranged thereon, each of the metal coils operable to produce a time-varying magnetic field in response to an applied signal, eyewear including one or more opaque surfaces for blocking a wearer's vision and a plurality of light-emitting diodes (LEDs) arranged on the eyewear so as to be directed toward the wearer's eyes, and a frequency generator coupled to the plurality of speakers, the plurality of metal coils, and the plurality of LEDs. The frequency generator may be operable to deliver respective frequency signals to simultaneously drive the plurality of speakers, the plurality of metal coils, and the plurality of LEDs.

The plurality of speakers may include four speakers. The four speakers may be arranged to face each other in two pairs defining two perpendicular axes. Each of the speakers may include a parabolic mirrored dish defined by a plurality of mirrors arranged in one or more spirals. The one or more spirals may comprise one or more Fibonacci spirals.

The plurality of metal coils may include three rows of metal coils extending in a longitudinal direction of the belt. Each of the three rows of metal coils may include four metal coils. The four metal coils in a first of the three rows may be respectively aligned, in a transverse direction of the belt, with the four metal coils of a second of the three rows and with the four metal coils of a third of the three rows.

The plurality of LEDs may include one or more LEDs arranged on the eyewear so as to be directed toward the wearer's left eye and one or more LEDs arranged on the eyewear so as to be directed toward the wearer's right eye.

The frequency generator may be operable to deliver eighteen unique frequencies simultaneously.

Another aspect of the embodiments of the present disclosure is a method of delivering stimulation to a subject. The method may comprise positioning a plurality of speakers so as to face a subject, the speakers capable of producing frequencies under 20 Hz, wrapping a belt around the subject, the belt including a plurality of metal coils arranged thereon so as to face the subject, each of the metal coils operable to produce a time-varying magnetic field in response to an applied signal, positioning eyewear on the subject, the eyewear including one or more opaque surfaces for blocking the subject's vision and a plurality of light-emitting diodes (LEDs) arranged on the eyewear so as to be directed toward the subject's eyes, and delivering, from a frequency generator, respective frequency signals to simultaneously drive the plurality of speakers, the plurality of metal coils, and the plurality of LEDs.

The plurality of speakers may include four speakers. The delivering of the respective frequency signals may include delivering a first set of four different frequency signals to respectively drive the four speakers to produce a first combination of four tones during a first period of the stimulation. The delivering of the respective frequency signals may include delivering a second set of four different frequency signals to respectively drive the four speakers to produce a second combination of four tones during a second period of the stimulation following the first period, at least one of the four speakers producing a different tone in the first combination than in the second combination. The four tones of the first combination may be the same as the four tones of the second combination. The delivering of the respective frequency signals may include delivering three or more sets of four different frequency signals to respectively drive the four speakers to produce three or more corresponding combinations of four tones successively during three or more corresponding periods of the stimulation. A frequency sum of the four tones of each successive combination may monotonically increase or decrease over the three or more periods. The frequency sum may monotonically increase over the three or more periods from below 60 Hz to above 200 Hz or monotonically decrease over the three or more periods from above 200 Hz to below 60 Hz. The individual frequencies of the tones may go up to 75 Hz.

The plurality of metal coils may include four metal coils. The delivering of the respective frequency signals may include delivering a first set of four different frequency signals to respectively drive the four metal coils to produce a first combination of four time-varying magnetic fields during a first period of the stimulation. The delivering of the respective frequency signals may include delivering a second set of four different frequency signals to respectively drive the four metal coils to produce a second combination of four time-varying magnetic fields during a second period of the stimulation following the first period, each of the four metal coils producing a different time-varying magnetic field in the first combination than in the second combination. The delivering of the respective frequency signals may include delivering three or more sets of four different frequency signals to respectively drive the four metal coils to produce three or more corresponding combinations of four time-varying magnetic fields successively during three or more corresponding periods of the stimulation. A frequency sum of the applied signals that produce the four time-varying magnetic fields of each successive combination may monotonically increase or decrease over the three or more periods. The frequency sum may monotonically increase over the three or more periods from below 1 Hz to above 140 Hz or monotonically decrease over the three or more periods from above 140 Hz to below 1 Hz. The individual frequencies may go up to 50 Hz.

The plurality of LEDs may include one or more LEDs arranged on the eyewear so as to be directed toward the subject's left eye and one or more LEDs arranged on the eyewear so as to be directed toward the subject's right eye. The delivering of the respective frequency signals may include delivering a first pair of frequency signals to respectively drive the one or more LEDs directed toward the subject's left eye and the one or more LEDs directed toward the subject's right eye LEDs to produce a first combination of two colors during a first period of the stimulation. The delivering of the respective frequency signals may further include delivering a second pair of frequency signals to respectively drive the one or more LEDs directed toward the subject's left eye and the one or more LEDs directed toward the subject's right eye LEDs to produce a second combination of two colors during a second period of the stimulation following the first period, at least one of the plurality of LEDs producing a different color in the first combination than in the second combination. The two colors of the first combination may be the same as the two colors of the second combination. The delivering of the respective frequency signals may include delivering three or more pairs of frequency signals to respectively drive the one or more LEDs directed toward the subject's left eye and the one or more LEDs directed toward the subject's right eye LEDs to produce three or more corresponding combinations of two colors successively during three or more corresponding periods of the stimulation. A frequency sum of flicker frequencies that produce the two colors of each successive combination may monotonically increase or decrease over the three or more periods. The individual flicker frequencies may go up to 100 Hz. Electromagnetic frequencies of the two colors may be octaves of corresponding frequency signals from among the pair of frequency signals.

The subject may be a human.

Another aspect of the embodiments of the present disclosure is a method of delivering stimulation to a subject. The method may comprise generating a plurality of frequency signals, generating a combination of audio tones according to the plurality of frequency signals, producing a time-varying magnetic field according to the plurality of frequency signals, producing colored light according to the plurality of frequency signals, and simultaneously directing the combination of audio tones, the time-varying magnetic field, and the colored light at the subject.

The subject may be a human.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The present disclosure encompasses various embodiments of systems, methods, and apparatuses for delivering restful and/or relaxing stimulation to a subject such as a human, non-human animal, or plant. The detailed description set forth below in connection with the appended drawings is intended as a description of several currently contemplated embodiments and is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
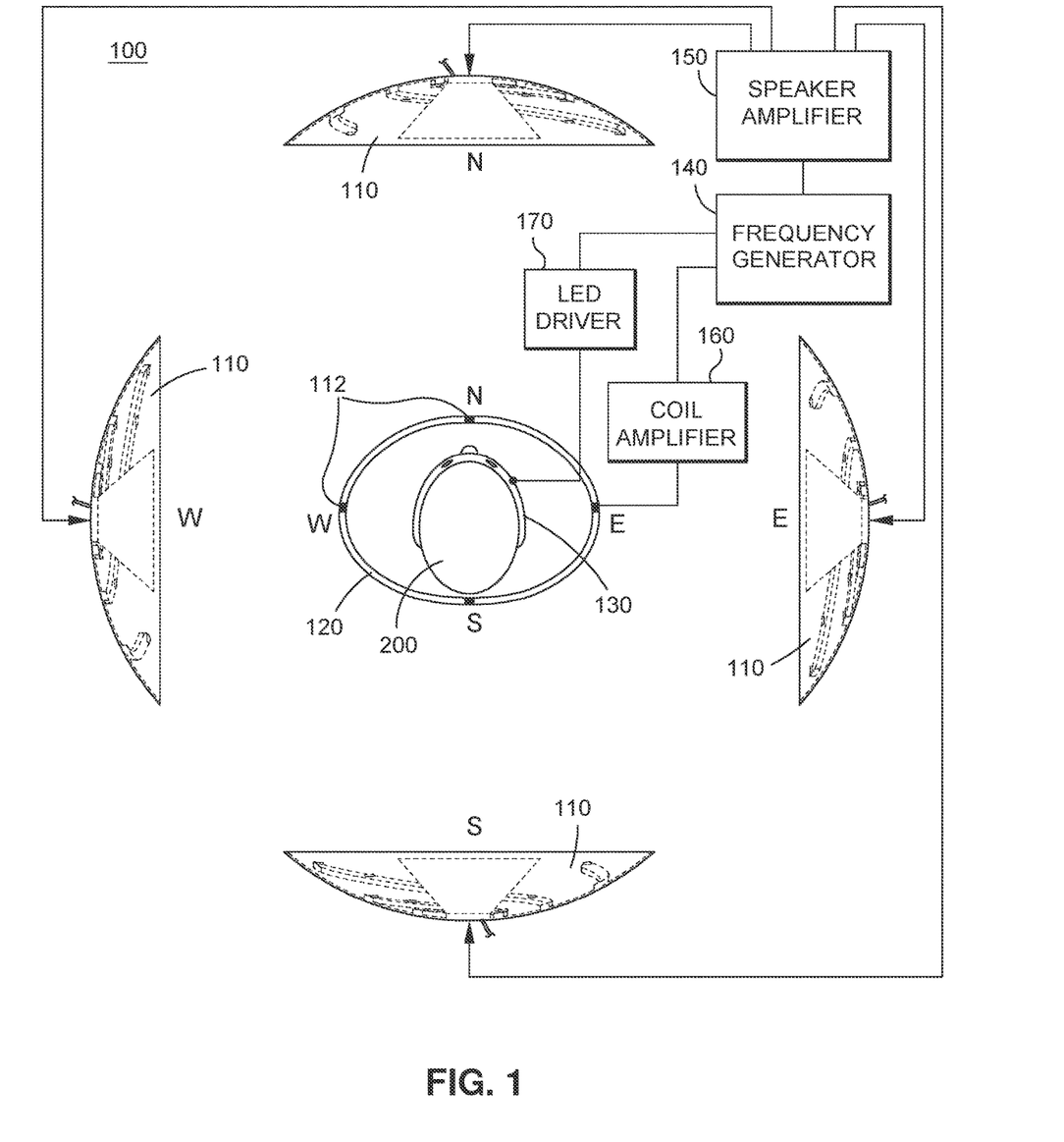
FIG. 1 shows a system for delivering stimulation to a subject according to an embodiment of the present disclosure.

FIG. 1 shows a system 100 for delivering stimulation to a subject 200 according to an embodiment of the present disclosure. In the illustrated example, the subject 200 is a human, but the subject 200 may be a non-human animal (such as a pet or wild animal), a plant, or any other living thing. The system 100 may function as a frequency propagating device designed to mimic the earth's natural magnetic fields generated by its rotation in space. In this regard, the system 100 may resound numerous and varying sine waves in source, frequency, intensity, and duration to create resonant musical harmonies in likeness to the earth resounding pulsed frequencies throughout all ecosystems supporting life. The system 100 may broadcast eighteen unique frequencies at the same time via three delivery systems: sound waves via speakers 110, pulsed electromagnetic fields via metal coils 122 included in a belt or wrap 120 to be worn by the subject 200, and visible light waves via light-emitting diodes (LEDs) 132 (see FIG. 5) arranged on eyewear 130 (in the case of a human or animal subject 200), all controlled by a single frequency generator 140. Each unique frequency (sound, magnetic field, or visible light) may represent an individual musical note which harmonizes with the other frequencies in combinations of major and minor musical chords and pulsed to the rate of the subject's heartbeat or other specified rate. The harmonic fields generated by the system 100 may have a balancing and regulating effect upon an organism, either animal or plant. The system 100 may further have a profound impact on sleep patterns, promoting balancing restful sleep in the subject 200.

The system 100 may include, in addition to the delivery systems (speakers 110, belt 120, and eyewear 130) and the frequency generator 140, any number of various amplifiers and drivers for driving the delivery systems according to the output of the frequency generator 140. In this regard, by way of example, FIG. 1 illustrates a speaker amplifier 150 operable to amplify one or more frequency signals output by the frequency generator 140 and drive the speakers 110 with the amplified signals (e.g., by driving a current through a voice coil thereof). In particular, the speaker amplifier 150 may simultaneously receive four frequency signals from the frequency generator, and each of the four frequency signals may be amplified by the speaker amplifier 150 to drive a respective one of four speakers 110 as shown. A coil amplifier 160 may similarly be provided, operable to amplify one or more frequency signals output by the frequency generator 140 and drive the metal coils 122 on the belt 120 with the amplified signals to produce a time-varying magnetic field directed toward the subject 200. For example, the coil amplifier 160 may receive and amplify four frequency signals, providing each of the four frequency signals to a respective one or to a respective group of metal coils 122 arranged to stimulate a corresponding region of the subject 200. An LED driver 170 may further be provided, operable to amplify one or more frequency signals output by the frequency generator 140 and drive the LEDs 132 (see FIG. 5) on the eyewear 130 with the amplified signals. As described in more detail below, for example, the LED driver 170 may control both the flicker rate and the color of the LEDs 132 according to the frequency signals output by the frequency generator 140.

Between the three delivery systems, a total of fifty-two frequencies may be broadcast over a single harmonic 9-minute session or a total of one hundred fifty-six frequencies may be broadcast over a three-part harmonic 27-minute session. The frequencies broadcast may range from 0.1075 Hz to 100 Hz. As described in more detail below, these musical harmonic sessions may commence with low frequencies and end with high frequencies in the AM for morning sessions, and they may commence with high frequencies and end with low frequencies in the PM for evening sessions.

Figures 2, 3:
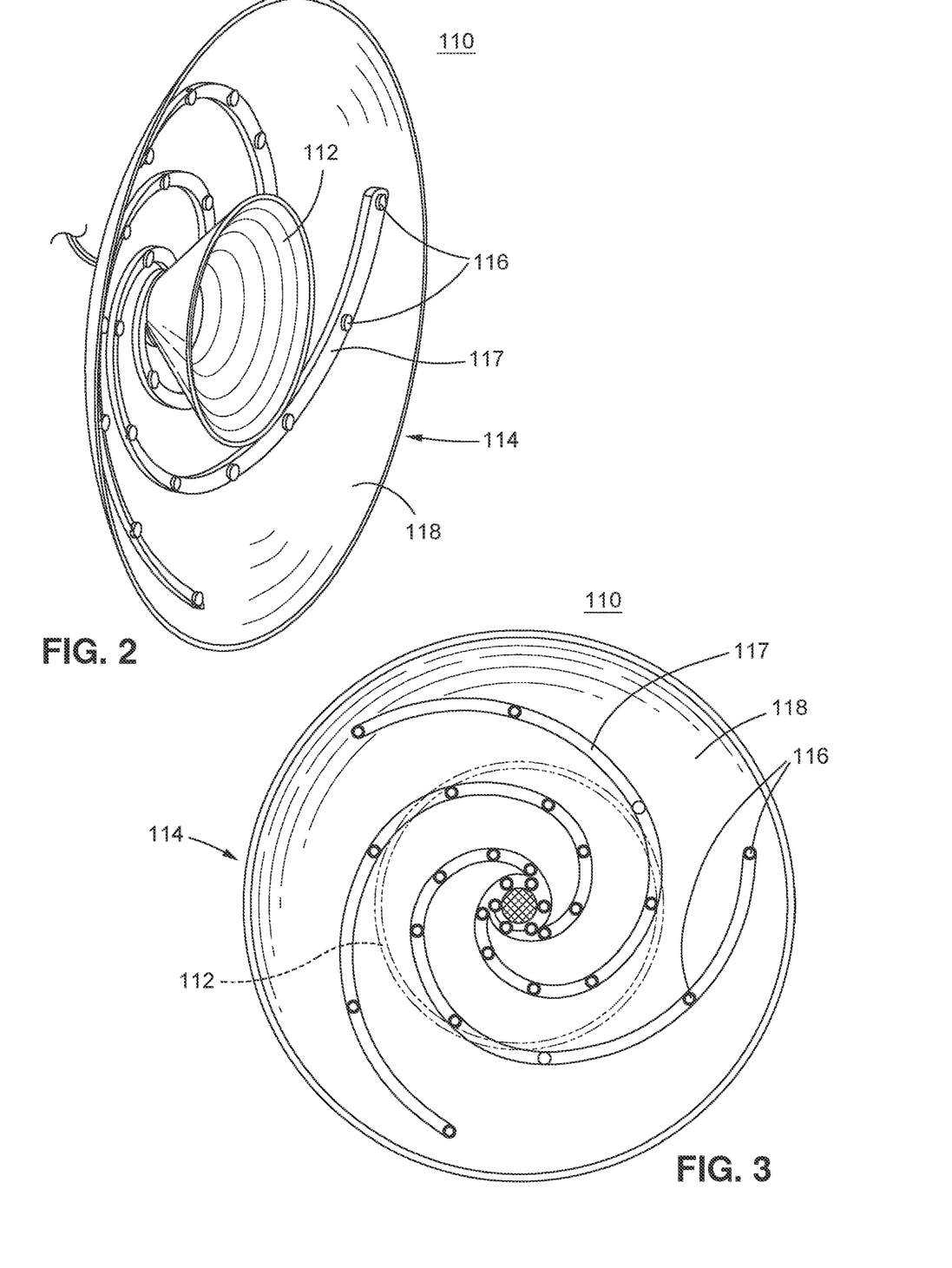
FIG. 2 shows a perspective view of a speaker.
FIG. 3 shows a front view thereof.

FIG. 2 shows a perspective view of one of the speakers 110, including a speaker cone 112 and a parabolic dish 114 surrounding the speaker cone 112. FIG. 3 shows a front view thereof, illustrating the parabolic dish 114 with the speaker cone 112 in phantom. The speaker 110 may be any conventional speaker capable of producing frequencies under 20 Hz and may be a subwoofer speaker, for example, except that the speaker 110 may differ from conventional speakers in that it may include a parabolic mirrored dish 114 that sits behind and surrounds the speaker cone 112 of the speaker 110. The parabolic mirrored dish 114 may be defined by a plurality of mirrors 116 arranged in one or more spirals, preferably Fibonacci spirals. In some implementations, the dish 114 may include only the mirrors 116 and mirror supports 117 for arranging the mirrors 116 in the one or more spirals, without including a backing 118 as is shown in the illustrated example. Each such speaker 110 may emit a sine wave sound frequency between 9-75 Hz. Each dish 114 may be between 12-18 inches in diameter, forming a "satellite" dish around the speaker sound-source. Within the dish 114, the spiral Fibonacci sequence pattern made of tiny mirrors 116 may be repeated to cover the entire dish 114, with the mirrors 116 spiraling to the perimeter of the dish 114 like a mosaic of mirrors in repeating spirals. It should be noted that the mirrors 116 may completely cover the dish 114 in some cases, or that the dish 114 may be made of mirrors 116. Just as a flashlight utilizes a metallic reflector cone to concentrate and reflect light, the parabolic mirrored dish 114 may similarly function to reflect the difficult-to-broadcast, ultra-low frequency sound waves. The ultra-low waves may be broadcast outwards following the pattern of the spiral shape, thereby condensing and concentrating the sound waves to focus the frequencies upon the subject 200.

In order to deliver the sound wave vibrational signature of the system 100, the plurality of speakers 110 may include four speakers 114, which may be arranged to face each other in two pairs defining two perpendicular axes. Collectively, the speakers 110 may thus deliver four separate tones from four separate speakers 110 placed at four corners of the subject 200. In particular, with the animal or plant subject 200 in the center, the speakers 110 (each including parabolic mirrored dish 114) may be set up on each side N, S, W, E of the subject 200 to form a crisscross pattern with each speaker 110 facing the subject 200 in the center.

The sine wave sound frequencies may be delivered via a particular sequence from the frequency generator 140, with each speaker 110 broadcasting a specific frequency. The four frequencies may combine partial major and minor musical chords to make a novel and unique musical chord referred to as a "harmonic" herein. Each complex chord within the programs ("Harmonic 3," "Harmonic 6," or "Harmonic 9," see below) may be played for three minutes as the speakers rotate the frequencies according to the table below over three octaves for a total of nine minutes. The complete program identified as "Harmonic 18" combines the Harmonic 3, Harmonic 6, and Harmonic 9 programs for a total of a 27-minute session to cover all the complex chord patterns as listed below within the frequencies of 9-75 Hz. In the AM (morning hours), the frequencies may preferably be played from low Hz to the higher Hz. In the PM (evening hours), the frequencies may preferably be played from high Hz to the lower Hz. The plurality of speakers 110 may be adjusted by a volume control that is separate from that of the other two delivery systems, allowing the intensity to be increased or decreased separate from the belt 120 or glasses 130.

Each harmonic listed in Tables 1, 2, and 3, below may be characterized by four separate musical note frequencies and may be considered a "pulse" lasting for one minute, totaling nine minutes per individual program session (consisting of nine harmonics) or totaling twenty-seven minutes for the complete "Harmonic 18" session. Each of the four values making up each harmonic is listed in Hz frequency below and represents a specific "note" as may be associated with a piano keyboard.

TABLE 1

Harmonic 3 (high to low)

| | Speaker N | Speaker S | Speaker W | Speaker E | Frequency Sum |
|---|---|---|---|---|---|
| Harmonic 3a | 39.04 | 44.8 | 55.04 | 66.56 | 205.44 |
| Harmonic 3b | 39.04 | 66.56 | 55.04 | 44.8 | 205.44 |
| Harmonic 3c | 39.04 | 55.04 | 66.56 | 44.8 | 205.44 |
| Harmonic 3q | 19.52 | 22.4 | 27.52 | 33.28 | 102.72 |
| Harmonic 3r | 19.52 | 33.28 | 27.52 | 22.4 | 102.72 |
| Harmonic 3s | 19.52 | 27.52 | 33.28 | 22.4 | 102.72 |
| Harmonic 3x | 9.76 | 11.2 | 13.76 | 16.64 | 51.36 |
| Harmonic 3y | 9.76 | 16.64 | 13.76 | 11.2 | 51.36 |
| Harmonic 3z | 9.76 | 13.76 | 16.64 | 11.2 | 51.36 |

TABLE 2

Harmonic 6 (low to high)

|  | Speaker N | Speaker S | Speaker W | Speaker E | Frequency Sum |
|---|---|---|---|---|---|
| Harmonic 6a | 10.24 | 11.68 | 14.72 | 17.6 | 54.24 |
| Harmonic 6b | 10.24 | 17.6 | 14.72 | 11.68 | 54.24 |
| Harmonic 6c | 10.24 | 14.72 | 17.6 | 11.68 | 54.24 |
| Harmonic 6q | 20.48 | 23.36 | 29.44 | 35.2 | 108.48 |
| Harmonic 6r | 20.48 | 35.2 | 29.44 | 23.36 | 108.48 |
| Harmonic 6s | 20.48 | 29.44 | 35.2 | 23.36 | 108.48 |
| Harmonic 6x | 40.96 | 46.72 | 58.88 | 70.4 | 216.96 |
| Harmonic 6y | 40.96 | 70.4 | 58.88 | 46.72 | 216.96 |
| Harmonic 6z | 40.96 | 58.88 | 70.4 | 46.72 | 216.96 |

TABLE 3

Harmonic 9 (high to low)

|  | Speaker N | Speaker S | Speaker W | Speaker E | Frequency Sum |
|---|---|---|---|---|---|
| Harmonic 9a | 42.88 | 48.64 | 62.72 | 74.24 | 228.48 |
| Harmonic 9b | 42.88 | 74.24 | 62.72 | 48.64 | 228.48 |
| Harmonic 9c | 42.88 | 62.72 | 74.24 | 48.64 | 228.48 |
| Harmonic 9q | 21.44 | 24.32 | 31.36 | 37.12 | 114.24 |
| Harmonic 9r | 21.44 | 37.12 | 31.36 | 24.32 | 114.24 |
| Harmonic 9s | 21.44 | 31.36 | 37.12 | 24.32 | 114.24 |
| Harmonic 9x | 10.72 | 12.16 | 15.68 | 18.56 | 57.12 |
| Harmonic 9y | 10.72 | 18.56 | 15.68 | 12.16 | 57.12 |
| Harmonic 9z | 10.72 | 15.68 | 18.56 | 12.16 | 57.12 |

In general, as shown in the above Tables 1, 2, and 3, the frequency generator 140 may deliver a first set of four different frequency signals (e.g., 39.04 Hz, 44.8 Hz, 55.04 Hz, 66.56 Hz in the case of Harmonic 3a) to respectively drive the four speakers 110 to produce a first combination of four tones during a first period of the stimulation. The frequency generator 140 may then deliver a second set of four different frequency signals (e.g., 39.04 Hz, 66.56 Hz, 55.04 Hz, 44.8 Hz in the case of Harmonic 3b) to respectively drive the four speakers 110 to produce a second combination of four tones during a second period of the stimulation following the first period, at least one of the four speakers 110 producing a different tone in the first combination than in the second combination. In this case, for example, the Speakers S and E produce different tones in the first combination than they do in the second combination. Namely, they swap the 44.8 Hz and 66.56 Hz tones with each other. It should be noted, as illustrated in the example of Harmonic 3a and Harmonic 3b, that the four tones of the first combination may be the same as the four tones of the second combination, even though one or more of the speakers 110 change tones. In this way, during each period of a given program session (e.g., Harmonic 3) the speakers 110 may produce another combination of tones, sometimes consisting of the same four tones but always shifting at least with respect to which speaker 110 produces which tone.

Taking the Harmonic 3 program as an example, the same four tones are cycled between the speakers 110 for the first three combinations (Harmonics 3a, 3b, and 3c), then a new set of four tones are similarly cycled between the speakers 110 for the next three combinations (Harmonics 3q, 3r, and 3s), and then a final set of four tones are cycled between the speakers 110 for the final three combinations (Harmonics 3x, 3y, and 3z). In this way, the frequency generator 140 may deliver three or more sets of four different frequency signals to respectively drive the four speakers 110 to produce three or more corresponding combinations of four tones successively during three or more corresponding periods of the stimulation (e.g., nine combinations during nine periods in the Harmonic 3 program of Table 1). Preferably, a frequency sum of the four tones of each successive combination may monotonically increase or decrease over the three or more periods. For example, in the case of the Harmonic 3 program, it can be seen that the frequency sum (shown in Table 1) of each successive combination (and equivalently the average) monotonically decreases, that is, either stays the same or decreases, without increasing. In this sense, the Harmonic 3 program may be regarded as a "high to low" program, preferably used in the evening. By way of contrast, the Harmonic 6 program may be regarded as a "low to high" program, preferably used in the morning, since the frequency sum monotonically increases as shown in Table 2. In general, as can be seen in Tables 1-3, the range of frequencies delivered via the four speakers 110 may be such that the frequency sum monotonically increases over the three or more periods from below 60 Hz to above 200 Hz or monotonically decreases over the three or more periods from above 200 Hz to below 60 Hz during the course of a given program session.

Figure 4:
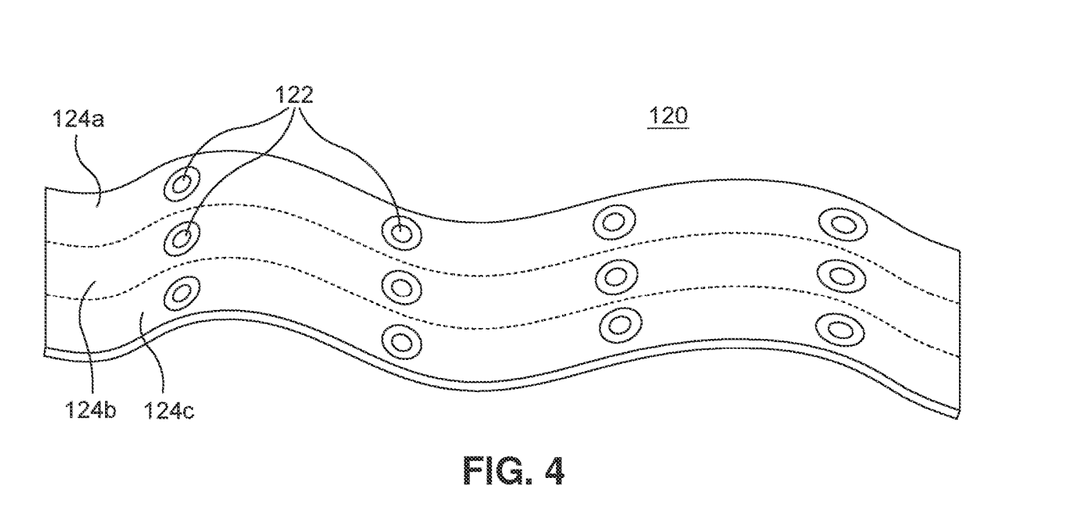
FIG. 4 shows a belt including metal coils.

FIG. 4 shows the belt 120 including a plurality of metal coils 122 arranged thereon. In order to deliver the pulsed magnetic field signature of the system 100, each of the metal coils 122 (which may be made of copper, for example) may be operable to produce a time-varying magnetic field in response to an applied signal. The belt 120 may be sized to wrap around a human subject's midsection (e.g., hips and/or waist and/or chest) and may be, for example, 35-50 inches long and 6-24 inches wide, preferably 12 inches wide, with the metal coils 122 concentrically wrapped in a spiral circle. The belt 120 may be sized differently for non-human subjects 200. The plurality of metal coils 122 may include three rows of metal coils 122 extending in the longitudinal direction of the belt 120. As shown in FIG. 4, for example, in which the belt 120 contains twelve metal coils 122, each of the three rows 124a, 124b, 124c may include four metal coils 122. The four metal coils 122 in the first row 124a may be respectively aligned, in the transverse direction of the belt 120, with the four metal coils 122 of the second row 124b and with the four metal coils 122 of the third row 124c. When the belt 120 is worn by the subject 200, the metal coils 122 may face the subject 200 such that the time-varying magnetic field(s) produced by the metal coils 122 may be directed into the body of the subject 200 at the same positions N, S, W, E of the subject 200 that are used for the placement of the speakers 110. It is contemplated that the belt/wrap 120 may have twelve sacred geometrical symbols (one placed over each metal coil 122) and may be wrapped so that the symbols face the treatment area of the subject 200.

Each of the metal coils 122 may emit the same musical notes (only harmonizing on a different octave) as the sine wave frequencies produced by the speakers 110. For example, a sinusoidal current applied to each metal coil 122 by the coil amplifier 160 (in response to the frequency signals generated by the frequency generator 140) may induce a time-varying magnetic field in each metal coil 122 that varies with the same frequency as the respective frequency signal, thus generating an electromotive force on the subject 200. The frequencies may be emitted in the same pattern as the above-described combination of major and minor chords. In particular, the frequencies may consist of nine octaves ranging from 0.1 Hz to 60 Hz as specifically listed in Tables 4-6 below. Each harmonic chord signature may be activated for one minute at the same time the corresponding speaker sound waves are toned, for three segments of three minutes each (e.g., Harmonic 3a-3c, Harmonic 3q-3s, and Harmonic 3x-3z) for a total of nine minutes per harmonic session (e.g., Harmonic 3, Harmonic 6, or Harmonic 9). For the complete "Harmonic 18" program session, each of the three harmonic program sessions may be toned over nine octaves or twenty-seven minutes to activate 108 different frequencies for the session (27 chords times 4 frequencies per chord).

TABLE 4

Harmonic 3 (high to low)

| | Coil N | Coil S | Coil W | Coil E | Frequency Sum |
|---|---|---|---|---|---|
| Harmonic 3a | 39.04 | 44.8 | 27.52 | 33.28 | 144.64 |
| Harmonic 3b | 19.52 | 22.4 | 13.76 | 16.64 | 72.32 |
| Harmonic 3c | 9.76 | 11.2 | 6.88 | 8.32 | 36.16 |
| Harmonic 3q | 4.88 | 5.6 | 3.44 | 4.16 | 18.08 |
| Harmonic 3r | 2.44 | 2.8 | 1.72 | 2.08 | 9.04 |
| Harmonic 3s | 1.22 | 1.4 | 0.86 | 1.04 | 4.52 |
| Harmonic 3x | 0.61 | 0.7 | 0.43 | 0.52 | 2.26 |
| Harmonic 3y | 0.305 | 0.35 | 0.215 | 0.26 | 1.13 |
| Harmonic 3z | 0.1525 | 0.175 | 0.1075 | 0.13 | 0.565 |

TABLE 5

Harmonic 6 (low to high)

| | Coil N | Coil S | Coil W | Coil E | Frequency Sum |
|---|---|---|---|---|---|
| Harmonic 6a | 0.16 | 0.1825 | 0.115 | 0.1375 | 0.595 |
| Harmonic 6b | 0.32 | 0.365 | 0.23 | 0.275 | 1.19 |
| Harmonic 6c | 0.64 | 0.73 | 0.46 | 0.55 | 2.38 |
| Harmonic 6q | 1.28 | 1.46 | 0.92 | 1.1 | 4.76 |
| Harmonic 6r | 2.56 | 2.92 | 1.84 | 2.2 | 9.52 |
| Harmonic 6s | 5.12 | 5.84 | 3.68 | 4.4 | 19.04 |
| Harmonic 6x | 10.24 | 11.68 | 7.36 | 8.8 | 38.08 |
| Harmonic 6y | 20.48 | 23.36 | 14.72 | 17.6 | 76.16 |
| Harmonic 6z | 40.96 | 46.72 | 29.44 | 35.2 | 152.32 |

TABLE 6

Harmonic 9 (high to low)

| | Coil N | Coil S | Coil W | Coil E | Frequency Sum |
|---|---|---|---|---|---|
| Harmonic 9a | 42.88 | 48.64 | 31.36 | 37.12 | 160 |
| Harmonic 9b | 21.44 | 24.32 | 15.68 | 18.56 | 80 |
| Harmonic 9c | 10.72 | 12.16 | 7.84 | 9.28 | 40 |
| Harmonic 9q | 5.36 | 6.08 | 3.92 | 4.64 | 20 |
| Harmonic 9r | 2.68 | 3.04 | 1.96 | 2.32 | 10 |
| Harmonic 9s | 1.34 | 1.52 | 0.98 | 1.16 | 5 |
| Harmonic 9x | 0.67 | 0.76 | 0.49 | 0.58 | 2.5 |
| Harmonic 9y | 0.335 | 0.38 | 0.245 | 0.29 | 1.25 |
| Harmonic 9z | 0.1675 | 0.19 | 0.1225 | 0.145 | 0.625 |

In general, as shown in the above Tables 4, 5, and 6, the frequency generator 140 may deliver a first set of four different frequency signals (e.g., 39.04 Hz, 44.8 Hz, 27.52, Hz, and 33.28 Hz in the case of Harmonic 3a) to respectively drive the four metal coils 122 of a given row 124*a*, 124*b*, or 124*c* to produce a first combination of four time-varying magnetic fields during a first period of the stimulation (the coils 122 of the other rows may duplicate the same frequencies, for example). The frequency generator 140 may then deliver a second set of four different frequency signals (e.g., 19.52 Hz, 22.4 Hz, 13.76 Hz, and 16.64 Hz in the case of Harmonic 3b) to respectively drive the four metal coils 122 to produce a second combination of four time-varying magnetic fields during a second period of the stimulation following the first period, each of the four metal coils 122 producing a different time-varying magnetic field (e.g., varying at a different frequency) in the first combination than in the second combination. During each period of a given program session (e.g., Harmonic 3) the metal coils 122 may produce another combination of time-varying magnetic fields.

In this way, the frequency generator 140 may deliver three or more sets of four different frequency signals to respectively drive the four metal coils 122 to produce three or more corresponding combinations of four time-varying magnetic fields successively during three or more corresponding periods of the stimulation (e.g., nine combinations during nine periods in the Harmonic 3 program of Table 4). Preferably, a frequency sum of the four time-varying magnetic fields of each successive combination may monotonically increase or decrease over the three or more periods. For example, in the case of the Harmonic 3 program, it can be seen that the frequency sum (shown in Table 4) of each successive combination monotonically decreases, with the Harmonic 3 program thus being regarded as a "high to low" program, preferably used in the evening as described above. By way of contrast, the Harmonic 6 program may be regarded as a "low to high" program, preferably used in the morning, since the frequency sum monotonically increases as shown in Table 5. In general, as can be seen in Tables 4-6, the range of frequencies delivered via the four magnetic coils 122 of a given row 124*a*, 124*b*, or 126*c* may be such that the frequency sum monotonically increases over the three or more periods from below 1 Hz to above 140 Hz or monotonically decreases over the three or more periods from above 140 Hz to below 1 Hz during the course of a given program session.

Additionally, the harmonic frequencies delivered by the metal coils 122 may be pulsed with the beat of the subject's heart rhythm or by selecting another pulse frequency option (e.g., "60 bpm," where the magnetic field pulses every second) according to a setting such as one of the following example levels 1 to 7.

At level one (1), an intensity of 0.05 gauss (5 microTesla) is pulsed every second or every beat of the heart to a maximum intensity of 1 gauss.

At level two (2), the intensity of 0.5 gauss is pulsed every second or every beat of the heart to a maximum intensity of 2 gauss.

At level three (3), the intensity of 1 gauss is pulsed every second or every beat of the heart to a maximum intensity of 3 gauss.

At level four (4), the intensity of 2 gauss is pulsed every second or every beat of the heart to a maximum intensity of 4 gauss.

At level five (5), the intensity of 3 gauss is pulsed every second or every beat of the heart to a maximum intensity of 5 gauss.

At level six (6), the intensity of 4 gauss is pulsed every second or every beat of the heart to a maximum intensity of 6 gauss.

At level seven (7), the intensity of 5 gauss is pulsed every second or every beat of the heart to a maximum intensity of 7 gauss.

If no pulse frequency is selected, there will be no pulsation in the field. Rather, the time-varying magnetic field may be maintained at the base gauss for the selected level.

Figure 5:
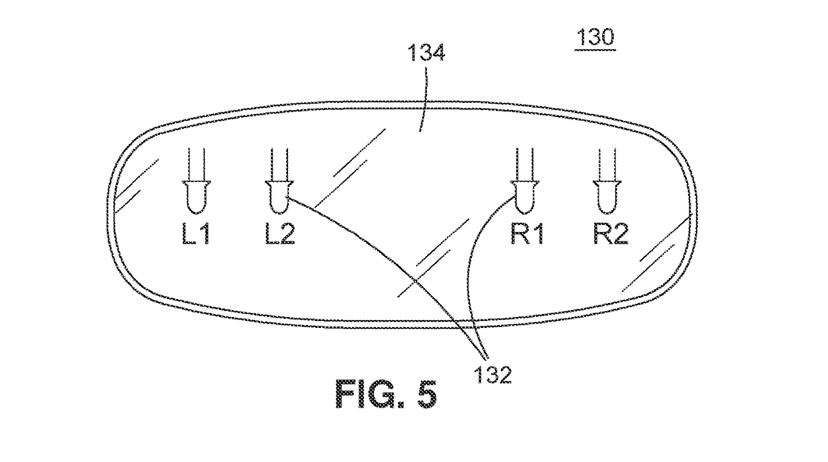
FIG. 5 shows eyewear including a plurality of light-emitting diodes (LEDs)

FIG. 5 shows eyewear 130 including a plurality of light-emitting diodes (LEDs) 132 arranged thereon so as to be directed toward the subject's eyes. In particular, the plurality of LEDs 132 may include one or more LEDs arranged so as to be directed toward the subject's left eye (indicated as "L1" and "L2" in FIG. 5) and one or more LEDs arranged so as to be directed toward the subject's right eye (indicated as "R1" and "R2" in FIG. 5). For example, there may be four left-eye LEDs L1, L2, L3, L4 and four right-eye LEDs R1, R2, R3, R3, with all of the left-eye LEDs functioning in unison and all of the right-eye LEDs functioning in unison. The eyewear 130 (e.g., a pair of white plastic solid glasses) may further include one or more opaque surfaces 134 for blocking the subject's vision, such as solid plastic opaque lenses that hold the LEDs 132. In order to deliver the visible light wavelength signature of the system 100, the LEDs 132 may produce a wavelength (color) corresponding to the "flicker" (frequency) of the current musical notes (harmonics) equally corresponding to that of the speakers 110 and the metal coils 122 in the belt 120. All delivery systems (speakers 110, belt 120, and eyewear 130) may be simultaneously broadcasting a different "octave" (i.e., frequency derived by doubling a base frequency) of the same musical notes.

As shown in Tables 7-9, below, a 9-minute session (e.g., Harmonic 3, Harmonic 6, or Harmonic 9) may include twelve 45-second periods grouped into six pairs (e.g., 3-1.1 and 3-1.2 being a first pair, 3-2.1 and 3-2.2 being a second pair, etc.), with each period defining right and left eye frequencies for driving LEDs 132 directed respectively at the right and left eyes (e.g., R1 and R2 directed at the right eye, L1 and L2 directed at the left eye). In a given period, the plurality of LEDs 132 directed at the same eye (which may be two as shown in FIG. 5 but may also be four, L1, L2, L3, L4, for example) may be illuminated at the same frequency. The right and left eye frequencies during the first period of a given pair may then swap during the second period of the pair. For example, in the Harmonic 3 program session (see Table 7), the right and left eye frequencies are respectively 89.6 Hz and 78.08 Hz in Harmonic 3-1.1 and then switch, after 45 seconds, to be 78.08 Hz and 89.6 Hz in Harmonic 3-1.2. In this way, after all six pairs of alternating right and left eye frequencies, the 9-minute session is finished.

TABLE 7

Harmonic 3 (high to low)

| | R | L | Frequency Sum |
|---|---|---|---|
| Harmonic 3-1.1 | 89.6 | 78.08 | 167.68 |
| Harmonic 3-1.2 | 78.08 | 89.6 | 167.68 |
| Harmonic 3-2.1 | 89.6 | 66.56 | 156.16 |
| Harmonic 3-2.2 | 66.56 | 89.6 | 156.16 |
| Harmonic 3-3.1 | 89.6 | 55.04 | 144.64 |
| Harmonic 3-3.2 | 55.04 | 89.6 | 144.64 |
| Harmonic 3-4.1 | 78.08 | 66.56 | 144.64 |
| Harmonic 3-4.2 | 66.56 | 78.08 | 144.64 |
| Harmonic 3-5.1 | 78.08 | 55.04 | 133.12 |
| Harmonic 3-5.2 | 55.04 | 78.08 | 133.12 |
| Harmonic 3-6.1 | 66.56 | 55.04 | 121.6 |
| Harmonic 3-6.2 | 55.04 | 66.56 | 121.6 |

TABLE 8

Harmonic 6 (low to high)

| | R | L | Frequency Sum |
|---|---|---|---|
| Harmonic 6-1.1 | 58.88 | 70.4 | 129.28 |
| Harmonic 6-1.2 | 70.4 | 58.88 | 129.28 |
| Harmonic 6-2.1 | 58.88 | 81.92 | 140.8 |
| Harmonic 6-2.2 | 81.92 | 58.88 | 140.8 |
| Harmonic 6-3.1 | 58.88 | 93.44 | 152.32 |
| Harmonic 6-3.2 | 93.44 | 58.88 | 152.32 |
| Harmonic 6-4.1 | 70.4 | 81.92 | 152.32 |
| Harmonic 6-4.2 | 81.92 | 70.4 | 152.32 |
| Harmonic 6-5.1 | 70.4 | 93.44 | 163.84 |
| Harmonic 6-5.2 | 93.44 | 70.4 | 163.84 |
| Harmonic 6-6.1 | 81.92 | 93.44 | 175.36 |
| Harmonic 6-6.2 | 93.44 | 81.92 | 175.36 |

TABLE 9

Harmonic 9 (high to low)

| | R | L | Frequency Sum |
|---|---|---|---|
| Harmonic 9-1.1 | 97.28 | 85.76 | 183.04 |
| Harmonic 9-1.2 | 85.76 | 97.28 | 183.04 |
| Harmonic 9-2.1 | 97.28 | 74.24 | 171.52 |
| Harmonic 9-2.2 | 74.24 | 97.28 | 171.52 |
| Harmonic 9-3.1 | 97.28 | 62.72 | 160 |
| Harmonic 9-3.2 | 62.72 | 97.28 | 160 |
| Harmonic 9-4.1 | 85.76 | 74.24 | 160 |
| Harmonic 9-4.2 | 74.24 | 85.76 | 160 |
| Harmonic 9-5.1 | 85.76 | 62.72 | 148.48 |
| Harmonic 9-5.2 | 62.72 | 85.76 | 148.48 |
| Harmonic 9-6.1 | 74.24 | 62.72 | 136.96 |
| Harmonic 9-6.2 | 62.72 | 74.24 | 136.96 |

In the above Tables 7, 8, and 9, the Hz frequency for driving a given LED 132 during a given period may determine a flicker frequency of the LED 132, that is, a frequency at which the LED 132 switches on and off. For example, in response to a frequency signal output by the frequency generator 140, the LED driver 170 may turn on and off the LED 132 at the frequency of the frequency signal. At the same time, the LED driver 170 may control the color of the given LED 132 based on the same frequency signal by setting the color to a color whose electromagnetic frequency (corresponding to wavelength in the visible range) is an octave of the frequency signal. For example, in the case of 89.6 Hz as used in the Harmonic 3 program (Table 7, above), the LED driver 170 may set the LED 132 to red (~395 THz) because 395 THz is approximately 42 octaves above 89.6 Hz (395 THz≈89.6 Hz*2^42). In this regard, Table 10, below, shows colors that may be selected by the LED driver 170 to correspond to the frequencies output by the frequency generator 140. The colors may be selected, for example, by adjusting the relative intensity of red, green, and blue LEDs that may be subcomponents of each of the LEDs 132 (e.g., by pulse width modulation). In this regard, multiple right-eye LEDs (e.g., R1, R2, R3, R4) or the multiple left-eye LEDs (e.g., L1, L2, L3, L4) may be regarded as these subcomponent LEDs, operable to produce red, green, blue, and white light, for example, in order to produce any desired color as a unit.

TABLE 10

| Frequency signal (Hz) | Color frequency (THz) | Color |
|---|---|---|
| 89.6 | 395 | Red |
| 78.08 | 685 | Violet |
| 66.56 | 585 | Aqua (Cyan) |
| 55.04 | 485 | Orange |
| 93.44 | 420 | Red |
| 81.92 | 720 | Violet |
| 70.4 | 620 | Blue |
| 58.88 | 520 | Yellow |
| 97.28 | 430 | Red |
| 85.76 | 780 | Violet |
| 74.24 | 650 | Blue |
| 62.72 | 550 | Green |

In general, as shown in the above Tables 7, 8, and 9, the frequency generator 140 may deliver a first pair of frequency signals (e.g., 89.6 Hz and 78.08 Hz in the case of Harmonic 3-1.1) to respectively drive the one or more LEDs 132 directed toward the subject's right eye (e.g., R1 and R2) and the one or more LEDs 132 directed toward the subject's left eye (e.g., L1 and L2) to produce a first combination of two colors during a first period of the stimulation (e.g., red and violet in the case of Harmonic 3-1.1). The frequency generator 140 may then deliver a second pair of frequency signals (e.g., 78.08 Hz and 89.6 Hz in the case of Harmonic 3-1.2) to respectively drive the one or more LEDs 132 directed toward the subject's right eye (e.g., R1 and R2) and the one or more LEDs 132 directed toward the subject's left eye (e.g., L1 and L2) to produce a second combination of two colors during a second period of the stimulation following the first period, at least one of the LEDs 132 producing a different color in the first combination than in the second combination. It should be noted, as illustrated in the example of Harmonic 3-1.1 and Harmonic 3-1.2, that the two colors of the first combination may be the same as the two colors of the second combination, even though one or more of the LEDs 132 change colors. In this way, during each period of a given program session (e.g., Harmonic 3) the LEDs 132 may produce another combination of colors, sometimes consisting of the same two colors but always shifting at least with respect to which LED 132 produces which color.

Taking the Harmonic 3 program as an example, the same two colors are alternated between the LEDs 132 for the first two 45-second periods (Harmonics 3-1.1 and 3-1.2), then a new set of two colors are similarly alternated between the LEDs 132 for the next two 45-second periods (Harmonics 3-2.1, 3-2.2), etc. In this way, the frequency generator 140 may deliver three or more pairs of frequency signals to respectively drive the one or more LEDs 132 directed toward the subject's right eye (e.g., R1 and R2) and the one or more LEDs 132 directed toward the subject's left eye (e.g., L1 and L2) to produce three or more corresponding combinations of two colors successively during three or more corresponding periods of the stimulation (e.g., twelve combinations during twelve periods in the Harmonic 3 program of Table 7). Preferably, a frequency sum of flicker frequencies that produce the two colors of each successive combination may monotonically increase or decrease over the three or more periods. For example, in the case of the Harmonic 3 program, it can be seen that the frequency sum (shown in Table 7) of each successive combination monotonically decreases, that is, either stays the same or decreases, without increasing. In this sense, the Harmonic 3 program may be regarded as a "high to low" program, preferably used in the evening. By way of contrast, the Harmonic 6 program may be regarded as a "low to high" program, preferably used in the morning, since the frequency sum monotonically increases as shown in Table 8.

Figure 6:
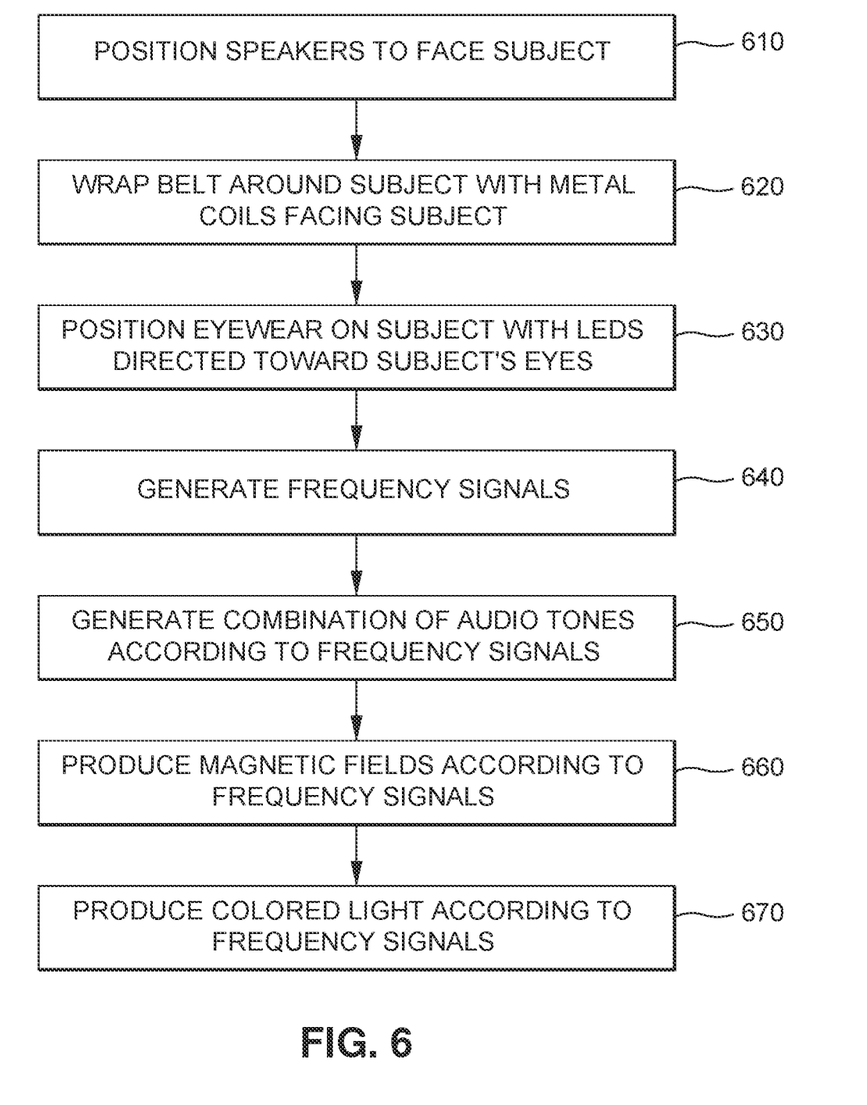
FIG. 6 shows an example operational flow according to an embodiment of the present disclosure.

FIG. 6 shows an example operational flow according to an embodiment of the present disclosure. The operational flow may be followed to provide a restful, relaxing, and/or therapeutic session to a subject 200 (such as the Harmonic 3, Harmonic 6, Harmonic 9, or Harmonic 18 programs described above), and in some cases to treat a health condition of the subject 200. As noted above, the subject 200 may be a human or non-human animal and may in some cases be a plant or other organism. Referring to the system 100 shown and described in relation to FIGS. 1-5 by way of example, the operational flow may begin with positioning speakers 110 to face the subject 200 (step 610), wrapping a belt or wrap 120 around the subject 200 having metal coils 122 facing the subject 200 (step 620), and positioning eyewear 130 on the subject 200 having LEDs 132 directed toward the subject's eyes (step 630). In the case of a subject 200 that is an organism that does not have eyes (such as a plant), the LEDs 132 may instead be directed at another part of the organism that is responsive to light (such as leaves), in which case the eyewear 130 may be omitted or replaced with any appropriate device for positioning the LEDs 132. Once the subject has been arranged as desired in relation to the three delivery systems of the system 100, the operational flow of FIG. 6 may continue with generating frequency signals using a frequency generator 140 (step 640) and, in response thereto, generating a combination of audio tones using the speakers 110 (step 650), producing magnetic fields using the metal coils 122 (step 660), and producing colored light using the LEDs 132 (step 670), all according to the frequency signals generated by the frequency generator 140 (in some cases with the same frequency signal simultaneously driving all three delivery systems).

As described above, the Harmonic 3, 6, and 9 programs may be regarded as "high to low" or "low to high" programs as shown in Tables 1-9. However, it is contemplated that any of the "high to low" programs may instead be reversed to serve as "low to high" programs and that any of the "low to high" programs may likewise be reversed to serve as "high to low" programs. In this way, any of the described programs may be used in the morning or the evening.

It is contemplated that the restful, relaxing, and/or therapeutic sessions described above may be further enhanced in a number of ways, for example, providing water to drink, such as a marble carafe of water that is "charged" overnight (e.g., by the natural attraction of the marble with the negatively charged fields of the earth and the associated ions) and drunk the next day, providing water topically, such as applying a formula of glacier and sea minerals to the skin morning and night, placing rose quartz on the perineum close to the pudendal nerve, providing a supplement for hormone balance such as a formula of plants and minerals compounded to enhance the receptivity of the body to the earths' natural fields, and/or instructing the subject 200 to perform light activity such as spinning slowly in a counter-clockwise direction three or more times before or after sessions to actively sensitize the body to the fields. In these ways, proper attraction of the constructive earth electromagnetic fields may be enhanced through optimizing the chemistry and physiology of the body of the subject 200.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A system for delivering stimulation to a subject, the system comprising:
 a plurality of speakers capable of producing frequencies under 20 Hz;
 a belt including a plurality of metal coils arranged thereon, each of the metal coils operable to produce a magnetic field in response to an applied signal;
 eyewear including one or more opaque surfaces for blocking a wearer's vision and a plurality of light-emitting diodes (LEDs) arranged on the eyewear so as to be directed toward the wearer's eyes; and
 a frequency generator coupled to the plurality of speakers, the plurality of metal coils, and the plurality of LEDs, the frequency generator operable to deliver respective frequency signals to simultaneously drive the plurality of speakers, the plurality of metal coils, and the plurality of LEDs.

2. The system of claim 1, wherein the plurality of speakers includes four speakers.

3. The system of claim 2, wherein the four speakers are arranged to face each other in two pairs defining two perpendicular axes.

4. The system of claim 1, wherein each of the speakers includes a parabolic mirrored dish defined by a plurality of mirrors arranged in one or more spirals.

5. The system of claim 4, wherein the one or more spirals comprise one or more Fibonacci spirals.

6. The system of claim 1, wherein the plurality of metal coils includes three rows of metal coils extending in a longitudinal direction of the belt.

7. The system of claim 6, wherein each of the three rows of metal coils includes four metal coils.

8. The system of claim 7, wherein the four metal coils in a first of the three rows are respectively aligned, in a transverse direction of the belt, with the four metal coils of a second of the three rows and with the four metal coils of a third of the three rows.

9. The system of claim 1, wherein the plurality of LEDs includes one or more LEDs arranged on the eyewear so as to be directed toward the wearer's left eye and one or more LEDs arranged on the eyewear so as to be directed toward the wearer's right eye.

10. The system of claim 1, wherein the frequency generator is operable to deliver eighteen unique frequencies simultaneously.

* * * * *